(12) United States Patent
Ali

(10) Patent No.: US 8,602,985 B2
(45) Date of Patent: Dec. 10, 2013

(54) SYSTEM AND METHOD TO ESTIMATE SIGNAL ARTIFACTS

(75) Inventor: Walid Ali, Croton-on-Hudson, NY (US)

(73) Assignee: Koninklijke Philips N.V., Eindhoven (NL)

( * ) Notice: Subject to any disclaimer, the term of this patent is extended or adjusted under 35 U.S.C. 154(b) by 2043 days.

(21) Appl. No.: 10/571,809

(22) PCT Filed: Oct. 6, 2004

(86) PCT No.: PCT/IB2004/051989
§ 371 (c)(1),
(2), (4) Date: Mar. 15, 2006

(87) PCT Pub. No.: WO2005/036440
PCT Pub. Date: Apr. 21, 2005

(65) Prior Publication Data
US 2007/0032705 A1    Feb. 8, 2007

Related U.S. Application Data

(60) Provisional application No. 60/510,174, filed on Oct. 10, 2003.

(51) Int. Cl.
*G06F 19/00* (2011.01)
*A61B 5/00* (2006.01)

(52) U.S. Cl.
CPC ........ *G06F 19/3406* (2013.01); *G06F 19/3418* (2013.01); *A61B 5/0002* (2013.01)
USPC .......................................... 600/300; 600/301

(58) Field of Classification Search
USPC .................. 600/300, 301; 128/903–905, 920
See application file for complete search history.

(56) References Cited

U.S. PATENT DOCUMENTS

| | | |
|---|---|---|
| 4,930,517 A | 6/1990 | Cohen et al. |
| 6,002,952 A | 12/1999 | Diab et al. |
| 6,069,975 A | 5/2000 | Lehmann et al. |
| 6,287,328 B1 * | 9/2001 | Snyder et al. ................. 600/509 |
| 2002/0016548 A1 | 2/2002 | Stadler et al. |
| 2002/0193670 A1 | 12/2002 | Garfield et al. |
| 2003/0023183 A1 * | 1/2003 | Williams ...................... 600/544 |
| 2003/0171661 A1 * | 9/2003 | Tong ............................. 600/300 |

FOREIGN PATENT DOCUMENTS

WO     WO03001997     1/2003

* cited by examiner

*Primary Examiner* — Bill Thomson
*Assistant Examiner* — Shirley Jian

(57) ABSTRACT

A method and system are disclosed that detect signal artifacts in one or more event signals. The system and method may be used to estimate whether a monitored signal includes artifacts based upon a statistical analysis using a transform function.

20 Claims, 1 Drawing Sheet

SYSTEM AND METHOD TO ESTIMATE SIGNAL ARTIFACTS

CROSS REFERENCE TO RELATED APPLICATION

Figure 1:
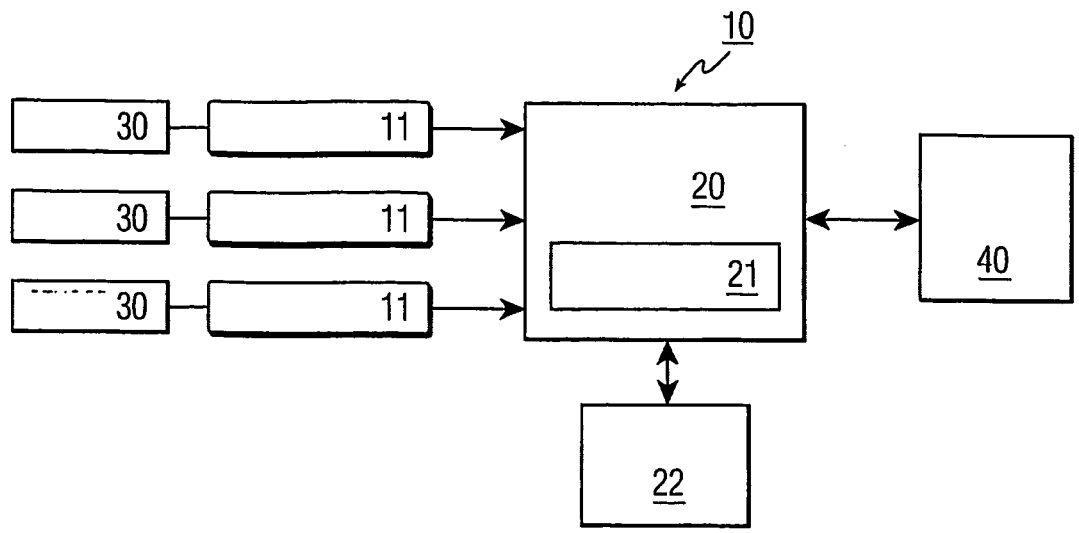

This application claims the benefit of U.S. provisional application Ser. No. 60/510,174 filed Oct. 10, 2003, which is incorporated herein by reference.

The present invention relates to a system and method for detecting signal artifacts, in particular, to system and a method used that estimates whether a monitored signal includes an artifact based upon a statistical analysis using a transform function.

One common problem associated with the use of measurement instruments is erroneous measurements that result from the introduction of an artifact signal into the event signal of interest. Typically, a measurement instrument detects one or more measured signals each comprised of the event signal of interest along with some level of artifact related to one or more non-event signals. The resulting measured signals can become significantly corrupted such that they should not be relied upon as an accurate representation of the event signal. Artifacts that corrupt the event signals can result from mechanical disturbances of sensors, electromagnetic interference, etc. As will be appreciated by those of skill in the art, the nature of the artifact signals will vary depending on the nature of the measuring instrument and the environmental conditions under which the measurements are taken.

One area in which the presence of artifact signals presents a potentially life-threatening problem is in the area of medical diagnostics and instrumentation. The appearance of a non-event signal in a patient monitoring device could result in a clinician making an incorrect decision with respect to a patient's treatment, or, for devices that use algorithms to make decisions, could result in the device itself making an incorrect assessment of the patient's condition.

In conventional patient monitoring systems, alarms are typically generated on crossing a limit or threshold in a signal being monitored, e.g., heart rate. While the threshold method is useful in determining physiological limits of variation of a parameter, it is not always the best method of event detection. The information that the clinician usually wants is the detection of relevant abnormalities or changes in a patient's condition. This is not easily reflected in a value crossing a limit, but rather by the simultaneous evolution of different parameters.

In practice, wide variations in a given parameter can be observed without any major alteration of the physiological function of a patient. Many of these fluctuations cause a false alarm in conventional patient monitoring systems. While the parameter being monitored did cross the limit, the alarm has no clinical significance. In such a case, for example, no major event is related to the worsening of the patient's status. As a result of this, many alarms in conventional patient monitoring systems are usually perceived as unhelpful by medical staff because of the high incidence of false alarms, i.e., alarms with no clinical significance.

As discussed above, conventional alarm techniques generate an alarm signal based on setting a threshold. For every parameter, the trigger of the alarm is set off immediately if its value reaches the limit or in some cases when its value has been beyond the limit for a given time. On the same patient monitoring system, when the values of several parameters are beyond the limit, an audible signal may be triggered on the first parameter that reached the alarm threshold; alternatively there can be a hierarchy of alarms. Generally, in all cases, it is necessary to set the threshold alarm limit.

Conventional patient monitoring systems provide for the setting of an alarm on most physiological data. In some cases, more than 40 alarm sources can be active, e.g., ventilation data, electrocardiogram, arterial pressure and pulse oximetry for a patient undergoing mechanical ventilation. In addition, perfusion pumps, nutrition pumps, automatic syringes and dialysis systems may also generate alarms.

False alarms may have several adverse consequences. A constant stream of false alarms may result in nurses delaying their intervention or trying to recognize life-threatening alarms by sound only. This practice may have severe consequences when the patient's condition is deteriorating.

What is needed is an improved method for detecting the presence and significance of artifact signals that may corrupt an event signal so that false alarms can be minimized.

The present invention is directed to a method and system for detecting signal artifacts. One aspect of the present invention is directed to a system and a method used with a patient monitoring apparatus where that apparatus estimates whether a patient's monitored signal includes artifacts based upon a statistical analysis.

One embodiment of the present invention is directed to a method for detecting a signal artifact in an event signal. The method including the steps of receiving at least two event signals, determining an estimated value of at least one of the at least two event signals using a transform function and at least the other of the at least two event signals, determining a deviation between the estimated event signal and the at least one event signal, and determining whether an artifact is present in the at least one event signal in accordance with the deviation.

Another embodiment of the present invention is directed to a device including a controller, a memory coupled to the controller, and an input interface arranged to received at least two event signals. The controller is arranged to determine an estimated value of at least one of the at least two event signals using a transform function and at least the other of the at least two event signals, and to determine a deviation between the estimated event signal and the at least one event signal, and to determine whether an artifact is present in the at least one event signal in accordance with the deviation.

Figure 2:
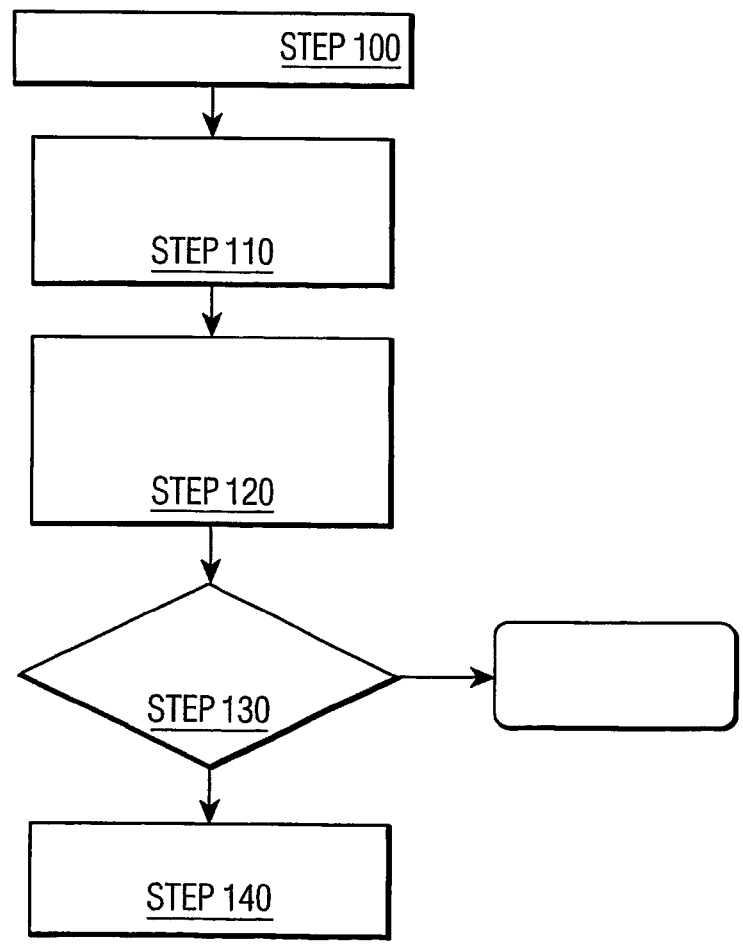

A more complete understanding of the method and apparatus of the present invention is available by reference to the following detailed description when taken in conjunction with the accompanying drawings wherein:

FIG. 1 depicts a diagram of a monitoring system according to an embodiment of the present invention; and FIG. 2 is a flow chart illustrating a method in accordance with one aspect of the present invention.

In the following description, for purposes of explanation rather than limitation, specific details are set forth such as the particular architecture, interfaces, techniques, etc., in order to provide a thorough understanding of the present invention. For purposes of simplicity and clarity, detailed descriptions of well-known devices, circuits, and methods are omitted so as not to obscure the description of the present invention with unnecessary detail.

FIG. 1 is a block diagram showing a system 10 according to one aspect of the present invention. One or more potentially corrupted event signals 11 are provided to a measurement device 20. The measurement device 20 includes a controller 21. The system 10 may also include a plurality of sensors 30 that obtain the event signals 11 and provide event signals 11 to the measurement system 20.

Several specific implementations of the system 10 are contemplated. For example, in one specific embodiment, the system 10 is a patient monitoring system capable of monitoring a plurality of patient parameters. Patient parameters include, but are not limited to, ECG, EEG, pulse, temperature, or any other biological activity. These patient parameters would be the event signals 11 of interest. In another more specific implementation, the system 10 is a defibrillator capable of measuring an ECG. In that instance, the ECG would be the event signal 11 of interest.

In another implementation, the measurement device 20 or the controller 21 is part of a server or a client in a client-servant network, e.g., the Internet.

As will be appreciated by those of skill in the art, the present invention is not limited to medical applications. The artifact detection techniques of the present invention can be used to detect artifact from any measured input signal source. For example, equipment that is used to measure ocean temperature, seismic activity, etc. can be set-up so that additional input signals are provided for signal processing and correlation with the signal of interest in order to determine whether the signal of interest has been corrupted with artifact. In addition, aspects of the present invention can be applied to systems that measure multiple event signals, wherein each event signal would employ this artifact detection method.

For purposes of illustration, an artifact detection technique in accordance with one embodiment of the present invention is described below in conjunction with patient monitoring equipment.

In this embodiment, one or more of patient event signals 11 ($x_1$, $x_2$, $x_3$, ..., $x_n$) are monitored. In this embodiment, the measurement device 20 is a patent monitoring system such as those used in an intensive care unit of a hospital. As one or more of the sensors 30 are connected to a patient, the event signals 11 start flowing into the measurement device 20. In this embodiment, the measurement device 20 includes a memory 21 for recording the input event signals 11.

For each of the plurality of patient event signals 11 an indicator for the presence of artifacts in each is needed. An estimation is established and its solution is used to detect any monitoring signal artifacts.

In this estimation, a signal y is assumed to be dependent on a number of other signals $x_1$, ..., $x_{n-1}$. No prior quantification for the dependency between the signal y the other signals $x_1$, ..., $x_{n-1}$ is needed.

The reason that the interactions may be studied without a detailed knowledge of the individual subsystems is that a complex system may be treated as a single unit or black-box about which nothing is known except for its stimulus (input) and response (output). By understanding the way a subsystem responds to a specific input, a mathematical description of that subsystem treated as a black-box may be developed. It so happens that, if the subsystem can be considered to have certain mathematical properties, the description developed for that one specific input is valid for all inputs.

For example, an understanding of the regulation of the physiology of the organism requires not only an understanding of each organ subsystem but also of their interactions. One difficulty is that each organ system is itself complex and any, in turn, consist of a large number of components. This complexity frequently makes a complete understanding of an organ subsystem impossible. However, the lack of understanding of the internal or fine-structure of an organ subsystem does not preclude an understanding of how that subsystem interacts with other organ subsystems.

This approach is reasonable in the study of physiological systems, and other systems, since it is actually only the stimuli and responses that are measured. For example, it is the heart rate (response) that is measured as a function of changes in arterial blood pressure (stimulus), and it is irrelevant that the functioning of the individual cell types of the heart cannot be determined. This systems approach to physiology has resulted in a greater understanding of the interactions between organ subsystems.

In the estimation, y is the real signal and $y_a$ is an estimated signal; ideally, $$\|y_a - y\| = 0 \tag{1}$$

It is noted that even if the dependency model to be estimated is non-linear, e.g., it is dependant on $x_1 x_2$, this parameter can be added as a new signal to be used for the estimation problem as $x_n$ and the set parameters to be used now for the estimation is $x_1$, ..., $x_n$. The relationship between the estimated signal $y_a$ and the monitored signals needed for the estimation $x_1$, ..., $x_n$ could be modeled as a transform function. A transfer function is a mathematical construct that relates the input of a system to its output. To determine the transfer function, it is necessary only to measure the input signal(s) and the output signal.

In the estimation, the transform can be expressed as T=[A] and the relationship between the estimated signal $$y_a = x[A] \tag{2}$$

Where [A] is a matrix of size n×1 and has elements ($a_1$, $a_2$, ..., $a_n$) and b (an estimation offset). The parameters ($a_1$, $a_2$, ..., $a_n$) must be determined to obtain the transfer function [A]. The only constraint for this estimation is having a fill rank [A] matrix, i.e., $\det\{[A]\} \neq 0$) and x is of size 1×n. It should be understood that x represents a matrix corresponding to the event signal(s) 11 ($x_1$, $x_2$, $x_3$, ..., $x_n$).

As mentioned above, this estimation can be recovered (estimated) by obtaining sample data (a variety of inputs x and corresponding outputs y). This yields a set of matched vertices, corresponding to a number of samples, by using a least square error (LSE) estimation method. If there are h correspondent vertex, i.e., $\{(x_1, y_1), ..., (x_h, y_h)\}$ and $\{(x_{a1}, y_{a1}), ..., (x_{ah}, y_{ah})\}$, where h>n+1, the relation can be obtained as the solution of the least square error (LSE) estimation which minimizes the LSE measure $$\sum_{i=1}^{h} \|y_{ai} - x_i[A]\|^2 \tag{3}$$

with respect to the unknown parameters ($a_1$, $a_2$, ..., $a_n$). The LSE solution is given by $$A = (X^T X)^{-1} X^T Y \tag{4}$$

Where X is of size h×n (h samples of n dimensions), Y is of size h×1

In the case of medical related applications, The MIT/BIH database (see http://www.physionet.org) may be used a source for the sample data needed to estimate the transformation matrix. For example, PhysioBank is a large and growing archive of well-characterized digital recordings of physiologic signals and related data for use by the biomedical research community. PhysioBank includes databases of multi-parameter cardiopulmonary, neural, and other biomedical signals from healthy subjects and patients with a variety of conditions with major public health implications, including sudden cardiac death, congestive heart failure, epilepsy, gait disorders, sleep apnea, and aging.

The MIT-BIH Polysomnographic Database is a collection of recordings of multiple physiologic signals during sleep. The database contains over 80 hours' worth of four-, six-, and seven-channel polysomnographic recordings, each with an ECG signal annotated beat-by-beat, and EEG and respiration signals annotated with respect to sleep stages and apnea. The physiological signals include electroencephalogram, electromyogram, electrooculogram, invasive blood pressure, respiratory wave, oxygen saturation, and cardiac volume as measured by VEST method.

The Massachusetts General Hospital/Marquette Foundation (MGH/MF) Waveform Database is a collection of electronic recordings of hemodynamic and electrocardiographic waveforms of patients in critical care units. The database consists of recordings from 250 patients and represents a broad spectrum of physiologic and pathophysiologic states. Individual recordings vary in length from 12 to 86 minutes, and in most cases are about an hour long. The recordings typically include three ECG leads, arterial pressure, pulmonary arterial pressure, central venous pressure, respiratory impedance, and airway CO2 waveforms. Some recordings include intra-cranial, left atrial, ventricular and/or intra-aortic-balloon pressure waveforms. ECG calibration, pressure zero, pressure calibration, and pressure/catheter frequency response tests are also recorded.

Once the estimated transformation matrix [A] is found, it may be used to predict the current value of the monitored signal y based on the current value of the remaining signals used for the estimation ($x_1, \ldots, x_n$) using equation (2). A measure of the discrepancy (equation 1) is an indication of a malfunction (e.g., an artifact) in the measured signal y.

Generally, if the measured signal y has a discrepancy greater than + or −5-15 percent from the calculated signal $y_a$, then the measured signal y includes an artifact. However, the exact range for a threshold deviation can be adjusted in accordance with known fluctuations in particular signals and/or normally observes ranges in such event signals. In addition, a lower or higher discrepancy threshold may be set depending on, for example, the severity of the clinical condition. A deviation below or equal to the threshold would indicate that an alarm in a patient monitoring system, for example, should be triggered.

The same process can be repeated for other event signals 11 to be able to predict more signals and monitor any presence of artifacts.

FIG. 2 is a flow chart showing an application of the various aspects of the present invention. The steps shown in FIG. 2 may be implemented by computer readable code executed by a data processing apparatus or controller 21. The code may be stored in a memory (e.g., memory 22) within the data processing apparatus (e.g., a patient bedside monitor) or read/downloaded from a memory medium such as a CD-ROM or floppy disk. In other embodiments, hardware circuitry may be used in place of, or in combination with, software instructions.

In step 100, two or more of the event signal(s) 11 are received. For example, in the patient monitoring system situation, event signals 11 are received for each patient to be monitored.

In step 110, an estimated event signal 11 (i.e., $y_a$) is determined using the transform [A] and other received event signals 11 (i.e., $X_1, X_2$, etc). The transform may be previously determined and stored, e.g., a look-up table. It is noted that multiple transforms for various event signals 11 to be estimated may be stored and/or accessible for use. In this regard, different transforms may be determined and stored for different population norms (e.g., adults verse children). The different transforms may be user selectable and/or a default transform may be used.

In step 120, the deviation between the measured event signal 11 and the estimated event signal is determined. If the deviation is within a predetermined threshold (step 130), an alarm indication may be provided in Step 140. This means that the measured event signal 11 does not include an artifact. If the deviation is greater and/or equal to the threshold, then an artifact is present.

While the preferred embodiments of the present invention have been illustrated and described, it will be understood by those skilled in the art that various changes and modifications may be made and equivalents may be substituted for elements thereof without departing from the true scope of the present invention. In addition, many modifications may be made to adapt to a particular situation and the teaching of the present invention without departing from the central scope. Therefore, it is intended that the present invention not be limited to the particular embodiment disclosed as the best mode contemplated for carrying out the present invention, but that the present invention include all embodiments falling within the scope of the appended claims.

The invention claimed is:

1. A device comprising:
   a controller;
   a memory coupled to the controller; and
   an input interface arranged to receive at least first and second event signals;
   wherein the controller is configured to:
      determine an estimated value of at least the first event signal using a transform function and the second event signal;
      determine a deviation between the estimated value and the first event signal,
      compare the deviation with a pre-determined threshold value, and
      determine whether an artifact is present in at least the first event signal in accordance with the comparison of the deviation and the pre-determined threshold value.

2. The device according to claim 1 wherein the device is a patient monitoring system.

3. The device according to claim 2 wherein the first and second event signals include patient monitored data signals.

4. The device according to claim 3 further comprising an alarm indicator coupled to the controller, the alarm indicator being triggered if no artifact was determined.

5. The device according to claim 1 further comprising a memory for recording at least first and second event signals.

6. The device according to claim 1, wherein the device is a server forming part of a client-server network.

7. The device according to claim 1, wherein the controller is further configured to:
   determine whether an artifact is present; and,
   determine a significance of the artifact.

8. A method for detecting a signal artifact in event signals, the method comprising:
   receiving at least first and second event signals with a control processor;
   with the control processor, determining an estimated value of at least the first event signal using a transform function and at least the second event signal;
   with the control processor, determining a deviation between the first event signal estimated value and the first event signal; and with the control processor, determining whether an artifact is present in at least the first event signal in accordance with the deviation.

9. The method according to claim 8, wherein the method is used with a patient monitoring system.

10. The method according to claim 9 wherein the at least first and second event signals are patient monitored data signals.

11. The method according to claim 10 further comprising: providing an alarm indication if no artifact was determined in the first event signal.

12. The method according to claim 8 further comprising: recording the at least first and second event signals.

13. The method according to claim 8, wherein the method is used in a server or client forming part of a client-server network.

14. The method according to claim 8 further including: comparing the determined deviation with a threshold and wherein determining whether an artifact is present is based on the comparing of the deviation and the threshold.

15. The method according to claim 8 further including: determining a significance of the artifact.

16. A control processor configured to perform the method according to claim 8.

17. A system for detecting a signal artifact in event signals, comprising:
means for receiving at least first and second event signals;
means for determining an estimated value of at least the first event signal using a transform function and at least the second event signal;
means for determining a deviation between the estimated value of the first event signal and the first event signal; and
means for determining whether an artifact is present in at least the first event signal in accordance with the deviation.

18. The system according to claim 17 wherein the system is a patient monitoring system.

19. The system according to claim 18 wherein the at least first and second event signals are patient monitored data signals.

20. The system according to claim 17 wherein the means for determining whether an artifact is present includes a means for comparing the determined deviation with a threshold.

* * * * *